United States Patent
Wang

(10) Patent No.: US 7,811,624 B1
(45) Date of Patent: Oct. 12, 2010

(54) SELF-ASSEMBLED LAYERS FOR ELECTRONIC DEVICES

(75) Inventor: Hailiang Wang, Camarillo, CA (US)

(73) Assignee: Dupont Displays, Inc., Santa Barbara, CA (US)

( * ) Notice: Subject to any disclaimer, the term of this patent is extended or adjusted under 35 U.S.C. 154(b) by 1157 days.

(21) Appl. No.: 11/305,139

(22) Filed: Dec. 16, 2005

Related U.S. Application Data

(60) Provisional application No. 60/640,394, filed on Dec. 30, 2004, provisional application No. 60/694,940, filed on Jun. 28, 2005.

(51) Int. Cl.
*B05D 5/06* (2006.01)

(52) U.S. Cl. .............. 427/64; 427/66; 427/74; 428/691; 428/696; 428/917

(58) Field of Classification Search .......... 427/64, 427/66, 74; 428/691, 696, 917
See application file for complete search history.

(56) References Cited

U.S. PATENT DOCUMENTS

| | | | |
|---|---|---|---|
| 6,303,238 B1 | 10/2001 | Thompson et al. | 428/690 |
| 2001/0019782 A1 | 9/2001 | Igarashi et al. | 428/690 |
| 2003/0087127 A1* | 5/2003 | Lee et al. | 428/690 |
| 2003/0162053 A1* | 8/2003 | Marks et al. | 428/690 |

FOREIGN PATENT DOCUMENTS

| EP | 1 191 612 A2 | 3/2002 |
|---|---|---|
| EP | 1 191 614 A2 | 3/2002 |
| WO | WO 00/70655 | 11/2000 |
| WO | WO 01/41512 A1 | 6/2001 |
| WO | WO 02/02714 A2 | 1/2002 |
| WO | WO 02/15645 A1 | 2/2002 |

OTHER PUBLICATIONS

Gustafsson, G. et al., "Flexible Light-Emitting Diodes made from Soluble Conducting Polymer", *Nature*, 1992, 357, 477-479.
O'Brien, D.F. et al., "Electrophosphoresence from a Doped Polymer Light Emitting Diode", *Synthetic Metals*, 2001, 116(1-3), 379-383.
Othmer, K., *Encyclopedia of Chemical Technology*, 1996, 18 ($4^{th}$ Ed), 837-860.

* cited by examiner

*Primary Examiner*—Binh X Tran
(74) *Attorney, Agent, or Firm*—Woodcock Washburn LLP

(57) ABSTRACT

Charge transport materials are provided, and methods for making the same.

8 Claims, 3 Drawing Sheets

US 7,811,624 B1

SELF-ASSEMBLED LAYERS FOR ELECTRONIC DEVICES

CROSS REFERENCE

This application claims the benefit of priority under 35 U.S.C. §119(e) from provisional U.S. Application Ser. Nos. 60/640,394, filed Dec. 30, 2004, and 60/694,940, filed Jun. 28, 2005, the disclosures of which are each incorporated herein by reference in their entireties.

FIELD

This disclosure relates generally to charge transport materials, for example, those found in organic electronic devices, and materials and methods for fabrication of the same.

BACKGROUND

Organic electronic devices convert electrical energy into radiation, detect signals through electronic processes, convert radiation into electrical energy, or include one or more organic semiconductor layers. Most organic electronic devices contain charge transport materials to facilitate migration of positive or negative charges through the organic device with relative efficiency and small loss of charges.

Thus, what is needed are additional charge transport materials.

SUMMARY

In one embodiment, charge transport materials are provided, and methods for making the same, as well as devices and sub-assemblies including the same.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

In one embodiment, compounds are provided having formula I:

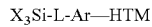

X$_3$Si-L-Ar—HTM            I wherein:
X is alkoxy or halogen;
L is either a bond or alkylene;
Ar is aryl; and
HTM is a hole transporting material.

Figure 1:
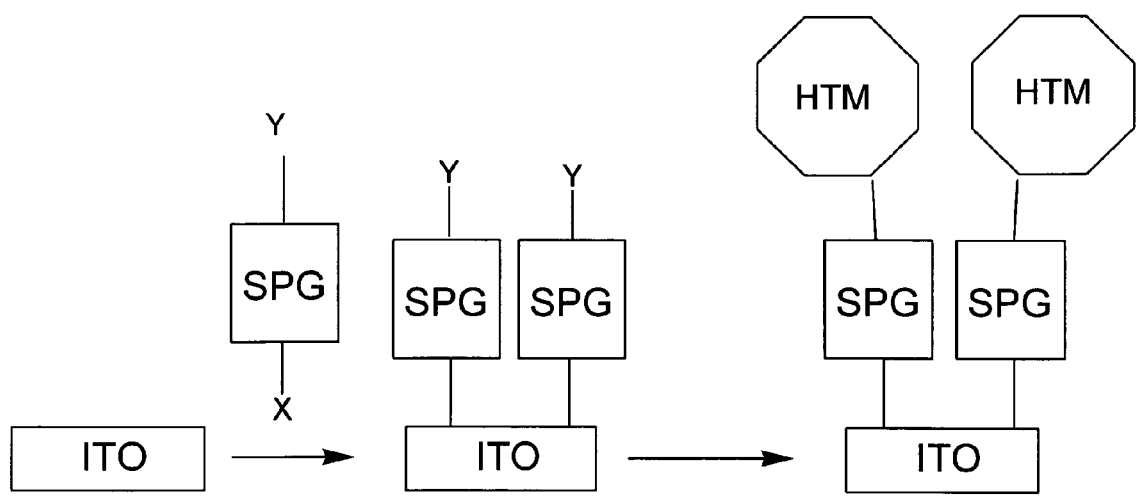
FIG. 1 is illustrates a schematic approach for producing self-assembled hole transport materials.
Figure 2:
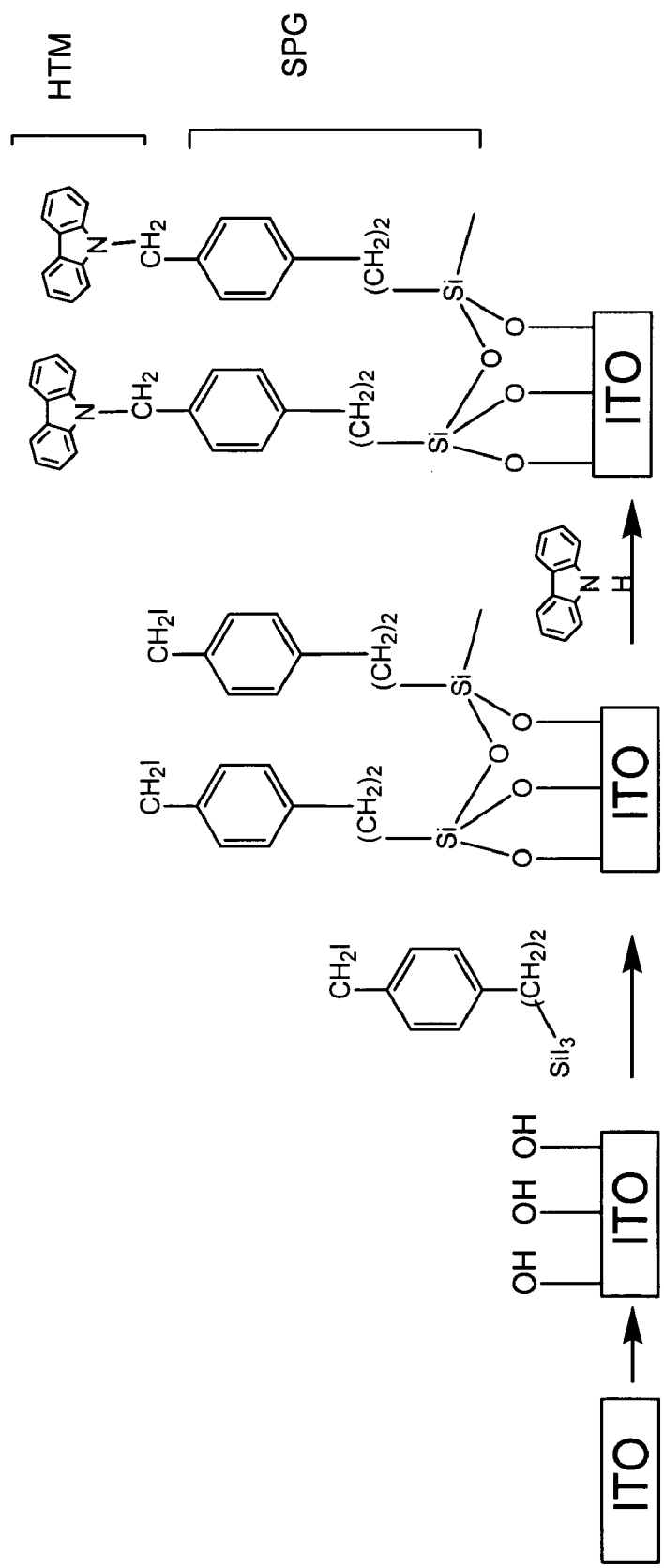
FIG. 2 illustrates an exemplary compound of the invention, and its use to form a layer on an indium/tin oxide surface.

In one embodiment, the compound is self-assembled. Chemical self-assembly of certain organic molecules provides a method for attaching hole transport materials to the surface of an electrode, for example, an anode. Devices utilizing these self-assembled compounds provide certain advantages over devices containing polymeric hole transport layers deposited from solution. For example, the devices using self-assembled compounds have increased thermal stability compared to devices containing multi-polymeric layer structures, which often suffer from inter-surface diffusion. In addition, the layers having self-assembled compounds typically have increased adhesion to an electrode surface, which contributes to increased charge transfer efficiency. A self-assembled hole transport layer can be attached to a surface as shown schematically in FIG. 1, where "ITO" refers to indium tin oxide, "SPG" refers to spacing group, "HTM" refers to hole transport molecule, and "X" and "Y" refer to function groups. It is well-established that an anode surface, such as ITO, contains surface hydroxyl groups. Choice of a spacer group having appropriate functional groups permits a self-assembled hole transport layer to be readily attached to the anode surface. In particular, FIG. 2 illustrates the preparation of an exemplary self-assembled hole transport layer according to one embodiment of the invention. First, a molecule bearing an iodosilyl moiety reacts with surface hydroxyl groups on the anode and is thereby covalently linked to the anode via siloxane bonds. Next, the iodomethyl functional group is utilized to attach the hole transport material, for example, carbazole. It is understood that a wide variety of molecules can be used to create layers of varying thickness. Indeed, the hole injection efficiency can be optimized by appropriate choice of spacer group and hole transport material. This method of attaching a hole transport material to an anode provides advantages relative to solution deposition of polymeric hole transport materials or vapor deposition of small molecule hole transport materials. For example, the layer is covalently bonded to the anode surface, resulting in a stable and thermally robust layer. Also, since the self-assembled hole transport layer is covalently bound to the anode surface, the adhesion of the layer to the surface is increased relative to a layer that is deposited onto the surface without forming a covalent bond.

Returning to the compound of formula I, in one embodiment, L is a C1 to C4 alkylene.

In one embodiment, Ar is phenyl. In one embodiment, Ar is further substituted.

HTM is any molecule having the ability to transport holes from an anode into an active layer in an electronic device. A wide variety of materials are contemplated for use as hole transport materials, including but not limited to, triphenylamines, heterocycles, stilbenes, hydrazones, oxadiazoles, phthalocyanines, and the like. In certain embodiments, the HTM is triphenylamine, for example, N,N'-dipheny-N,N'-di (3-methylphenyl)-1,1'-diphenyl-4,4'-diamine, N,N'-diphenyl-N,N'-dinaphthyl-1,1'-diphenyl-4,4-diamine, and the like. In one embodiment, HTM comprises a triphenylamine, a heterocycle, a stilbene, a hydrazone, an oxadiazole, or a phthalocyanine. In one embodiment, the HTM is N,N'-dipheny-N,N'-di(3-methylphenyl)-1,1'-diphenyl-4,4'-diamine, N,N'-diphenyl-N,N'-dinaphthyl-1,1'-diphenyl-4,4'-diamine, or combinations thereof. In other embodiments, the HTM is a heterocycle, for example, carbazole. Other embodiments include the HTM as a stilbene, hydrazone, oxadiazole, phthalocyanine, and the like.

In some embodiments, there are provided organic electronic devices including: an anode; a hole transporting layer; an active layer; an electron transporting layer; a cathode; and a self-assembled layer interposed between the anode and the hole transporting layer, wherein the self-assembled layer has the structure of Formula I, wherein X is alkoxy or halogen; L is either a bond or a $C_1$ to $C_6$ alkylene; Ar is a substituted or unsubstituted $C_6$ to $C_{22}$ aromatic group, and HTM is a moiety having hole transporting ability.

In another embodiment, there are provided methods for producing an organic electronic device. Such methods can be performed for example, by depositing an anode onto a substrate; depositing onto the anode a self-assembled layer having the structure according to Formula I; depositing a hole transport layer onto the self-assembled layer, depositing an active layer onto the hole transport layer, and depositing a cathode, thereby producing an organic electronic device.

In one embodiment, compositions are provided comprising the above-described compounds and at least one solvent, processing aid, charge transporting material, or charge blocking material. These compositions can be in any form, including, but not limited to solvents, emulsions, and colloidal dispersions.

Device

Figure 3:
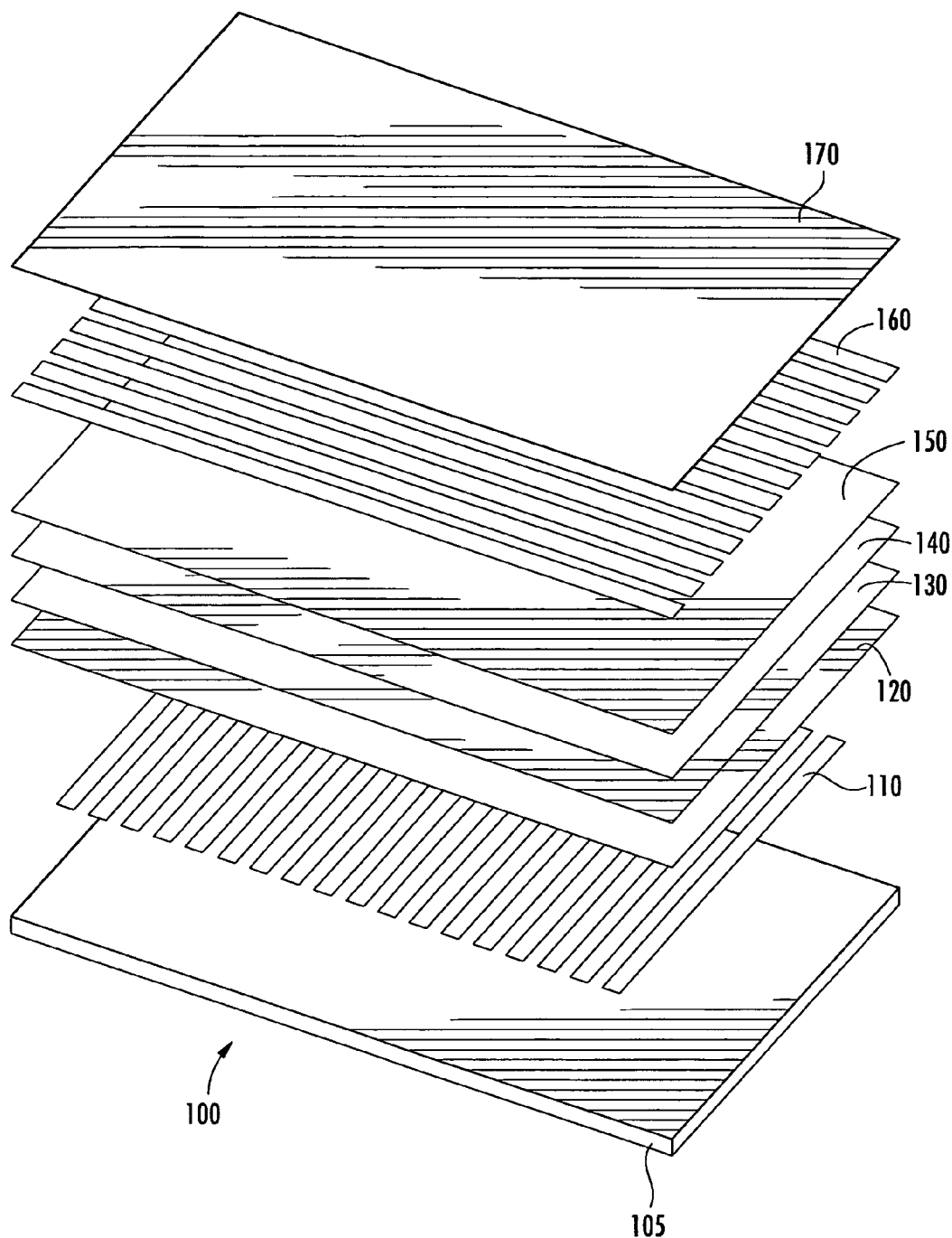
FIG. 3 a schematic diagram of an organic electronic device.

Referring to FIG. 3, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8, 10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer, Nature* 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 (4$^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino) phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p(diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino) styryl]-5-[p-(diethylamino)phenyl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3), cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or band-gap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

DEFINITIONS

The use of "a" or "an" are employed to describe elements and components of the invention. This is done merely for convenience and to give a general sense of the invention. This description should be read to include one or at least one and the singular also includes the plural unless it is obvious that it is meant otherwise.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

The invention claimed is:

1. A compound having formula I:

$$X_3Si\text{-}L\text{-}Ar\text{—}HTM \qquad\qquad I$$

wherein:
X is alkoxy or halogen;
L is either one bond or alkylene;
Ar is aryl; and
HTM is a hole transporting material selected from triphenylamine, a heterocycle, a stilbene, a hydrazone, an oxadiazole, and a phthalocyanine;
with the proviso that when L is alkylene, HTM is a triphenylamine selected from N,N'-dipheny-N,N'-di(3-methylphenyl)-1,1'-diphenyl-4,4'-diamine, N,N'-diphenyl-N,N'-dinaphthyl-1,1'-diphenyl-4,4'-diamine, and combinations thereof.

2. The compound of claim 1, wherein the compound is self-assembled.

3. The compound of claim 1, wherein Ar is further substituted.

4. The compound of claim 1, wherein Ar is phenyl.

5. The compound of claim 1, wherein L is a C1 to C4 alkylene.

6. A composition including the compound of claim 1.

7. An organic electronic device having an active layer including the compound of claim 1.

8. An article useful in the manufacture of an organic electronic device, comprising the compound of claim 1.

* * * * *